US007317006B2

(12) United States Patent
Hanssen et al.

(10) Patent No.: US 7,317,006 B2
(45) Date of Patent: Jan. 8, 2008

(54) THIENO[2,3-D]PYRIMIDINES WITH COMBINED LH AND FSH AGONISTIC ACTIVITY

(75) Inventors: Robert Gerard Jules Marie Hanssen, Oss (NL); Cornelis Marius Timmers, Oss (NL)

(73) Assignee: N.V. Organon, Oss (NL)

( * ) Notice: Subject to any disclaimer, the term of this patent is extended or adjusted under 35 U.S.C. 154(b) by 254 days.

(21) Appl. No.: 10/488,482

(22) PCT Filed: Aug. 29, 2002

(86) PCT No.: PCT/EP02/09647

§ 371 (c)(1),
(2), (4) Date: Feb. 26, 2004

(87) PCT Pub. No.: WO03/020726

PCT Pub. Date: Mar. 13, 2003

(65) Prior Publication Data

US 2004/0180873 A1 Sep. 16, 2004

(30) Foreign Application Priority Data

Sep. 4, 2001 (EP) .................................. 01203327

(51) Int. Cl.
*C07D 417/12* (2006.01)
*C07D 413/12* (2006.01)
*C07D 495/04* (2006.01)
*C07D 487/04* (2006.01)
*A61K 31/541* (2006.01)
*A61K 31/5355* (2006.01)
*A61K 31/519* (2006.01)
*A61K 31/496* (2006.01)
*A61K 31/381* (2006.01)
*A61P 5/08* (2006.01)

(52) U.S. Cl. ..................... 514/228.5; 544/60; 544/117; 544/278; 514/234.2; 514/260.1; 514/252.16

(58) Field of Classification Search ................ 544/278, 544/117, 60; 514/228.5, 234.2, 260.1, 252.16
See application file for complete search history.

(56) References Cited

FOREIGN PATENT DOCUMENTS

EP 0303306 2/1989
WO 0061586 10/2000

OTHER PUBLICATIONS

Abd-Elfattah et al., "Reactions With α-Substituted Cinnamonitriles," *Tetrahedron* 39 (1983) 3197-3199.
Abdel-Hady et al., "Syntheses of Some Thieno[2,3-d]Pyrimidines," *Sulfur Lett.* 9 (1989) 101-108.
Carabateas et al., "1-Ethyl-1,4-dihydro-4-oxo-7-(pyridinyl)-3-quinolinecarboxylic Acids. I. Synthesis of 3- and 4-(3-Aminophenyl)pyridine Intermediates," *J. Heterocyclic Chem. 21* (1984) 1849-1856.

Dorrington et al, "Effects of FSH on Gonadal Functions," *Recent Prog. Horm. Res.* 35 (1979) 301-342.
Heilbron et al., "Arylpyridines. Part IV. 3- and 4-Pyridyldiphenyls," *J. Chem. Soc.* (1940) 1279-1284.
Hussain et al., "A One Step Synthesis of 2-Methylthio-6-oxopyrimidine Derivatives: Preparation of Fused Pyrimidinones," *J. Heterocyclic Chem.* 22 (1985) 169-171.
Insler, V., "Gonadotropin Therapy: New Trends and Insights," *Int. J. Fertil.* 33 (1988) 85-97.
Jia et al., "Expression of Human Luteinizing Hormone (LH) Receptor: Interaction with LH and Chorionic Gonadotropin from Human but not Equine, Rat, and Ovine Species," *Mol. Endo.* 5 (1991) 759-768.
Kambe et al., "A One-Step Synthesis of 4-Oxo-2-thioxopyrimidine Derivatives by the Ternary Condensation of Ethyl Cyanoacetate, Aldehydes, and Thiourea," *Synthesis* (1979) 287-289.
Lévy et al., "The Role of LH in Ovarian Stimulation," *Human Reproduction* 15 (2000) 2258-2265.
Lu et al., "Effects of amphotericin B and ketoconazole on mouse oocyte maturation: implications on the role of meiosis-activating sterol," *Mol. Cell Endocrinol.* 164 (2000) 191-196.
Mannaerts et al., "Applications of In Vitro Bioassays for Gonadotrophins," *Neuro-endocrinology of Reproduction.* Ed. R. Rolland et al. (1987) 49-58.
Morse et al., Heterogeneity of Proteins in Commercial Preparations of Human Chorionic Gonadotropin (hCG) Demonstrated by Western Blotting, *Amer. J. Reproduct. Immunol. and Microbiology 17* (1988) 134-140.
Navot et al., "The Use of Follicle-Stimulating Hormone for Controlled Ovarian Hyperstimulation in in Vitro Fertilization," *J. In Vitro Fert. Embryo Transfer* 5 (1988) 3-13.
Nayudu, et al., "Factors Influencing the Rate of Preantral and Antral Growth of Mouse Ovarian Follicles in vitro," *J. Reprod. Fert. 95* (1992) 349-362.

(Continued)

*Primary Examiner*—Brenda L. Coleman
*Assistant Examiner*—Susanna Moore
(74) *Attorney, Agent, or Firm*—Susan Hess

(57) ABSTRACT

The invention relates to thieno[2,3-d]pyrimidine derivatives according to general formula I, or a pharmaceutically acceptable salt thereof,

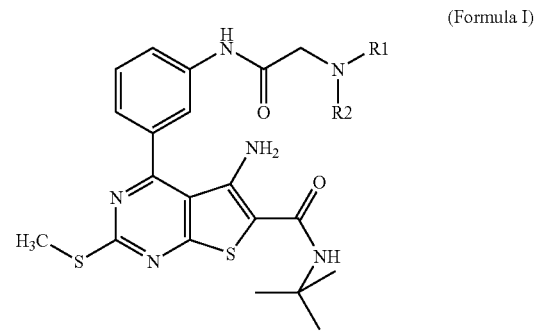

(Formula I)

wherein N(R1)R2 are joined in a (2-6C)heterocycloalkyl ring. The compounds of the invention have LH as well as FSH receptor activating activity and can be used in fertility regulating therapies.

14 Claims, No Drawings

OTHER PUBLICATIONS

Santilli et al., "Thieno[2,3-d]pyrimidines. I. A New Method for the Preparation of Esters and Amides of Thieno[2,3-d]pyrimidine-6-carboxylic Acids," *J. Heterocyclic Chem.* 8 (1971) 445-453.

Sharp, R.M., "Intratesticular Control of Steroidogenesis," *Clin. Endocrinol.* 33 (1990) 787-807.

Stratowa, et al., "Use of a Luciferase Reporter System for Characterizing G-Protein-Linked Receptors," *Curr. Opin. Biotech.* 6 (1995) 574-581.

Tumkevičius, S., "A Facile Synthesis of 5H-1-Thia-3,5,6,8-tetraazaacenaphthylenes," *Liebigs. Ann.* 9 (1995) 1703-1705.

Van Damme et al., "An Improved In Vitro Bioassay Method for Measuring Luteinizing Hormone (LH) Activity Using Mouse Leydig Cell Preparations," *Acta Endocrinol.* 77 (1974) 655-671.

THIENO[2,3-D]PYRIMIDINES WITH COMBINED LH AND FSH AGONISTIC ACTIVITY

CROSS-REFERENCE TO RELATED APPLICATIONS

This application is the national phase application under 35 U.S.C. § 371 of PCT International Application No. PCT/EP02/09647, which has an International filing date of Aug. 29, 2002, and which designated European Patent Office Application Serial No. 01203327.0, filed Sep. 4, 2001, as priority.

The invention relates to compounds having glycoprotein hormone agonistic activity, in particular to compounds having both Luteinizing Hormone (LH) and Follicle Stimulating Hormone (FSH) agonistic activity. The invention furthermore relates to pharmaceutical compositions containing the same as well as to the use of these compounds in medical therapy, particularly for use as a control of fertility.

Gonadotropins serve important functions in a variety of bodily functions including metabolism, temperature regulation and the reproductive process. The hypophyseal gonadotropins FSH and LH for example play a pivotal role in the stimulation of follicle development and maturation whereas LH is involved in induction of the ovulatory process (Sharp, R. M. Clin. Endocrinol 33, 787-807, 1990; Dorrington and Armstrong, Recent Prog. Horm. Res 35, 301-342, 1979; Levy et al, Human Reproduction 15, 2258-2265, 2000).

Currently, LH is applied clinically, in combination with FSH, for ovarian stimulation i.e. ovarian hyperstimulation for in vitro fertilisation (IVF) and induction of ovulation in infertile anovulatory women (Insler, V., Int. J. Fertility 33 85-97, 1988, Navot and Rosenwaks, J. Vitro Fert. Embryo Transfer 5, 3-13, 1988), as well as for male hypogonadism and male infertility.

Gonadotropins act on specific gonadal cell types to initiate ovarian and testicular differentiation and steroidogenesis. The actions of these pituitary and placental hormones are mediated by specific plasma membrane receptors that are members of the large family of G-protein coupled receptors. They consist of a single polypeptide with seven transmembrane domains and are able to interact with the Gs protein, leading to the activation of adenyl cyclase.

Gonadotropins destined for therapeutic purposes can be isolated from human urine sources and are of low purity (Morse et al, Amer. J. Reproduct. Immunol. and Microbiology 17, 143, 1988). Alternatively, they can be prepared as recombinant gonadotropins. In addition to these proteins, gonadotropin receptors can be activated or deactivated by synthetic low molecular weight compounds. Bicyclic heteroaromatic compounds have been described in WO 00/61586. By in vitro and in vivo experiments they are shown to be useful as LH agonists.

In normal females the release of pituitary LH and FSH is characterized by a mid-cycle surge which precedes the ovulation. Ovulation is characterized by three distinct physiological phenomena i.e. oocyte maturation, follicular rupture and luteinization. While the role of the LH-surge in the in vivo induction of these phenomena is undisputed, the role of the FSH-surge is less clear. However, it has been shown recently that FSH induces oocyte maturation in vitro by inducing cumulus cells to produce a factor that positively overcomes hypoxanthine induced meiotic arrest (Lu et al, Mol. Cell. Endocrinol. 164, 191-196, 2000). This factor is thought to be a meiosis activating sterol (MAS).

In ovulation induction, it is desirable to provide the effects of LH as the major component. According to the present invention compounds have been found with particular advantageous properties when used in protocols for enhanced fertility. In these compounds LH activity is accompanied by a FSH activity.

Thus the present invention provides low molecular weight compounds that in addition to LH activity unexpectedly also have FSH activity. In general these compounds are thieno[2,3-d]pyrimidines which at the 4-position of the pyrimidine ring are substituted by a phenyl group which in turn is substituted at the meta position.

The present invention resides in thieno[2,3-d]pyrimidine derivatives according to general formula I,

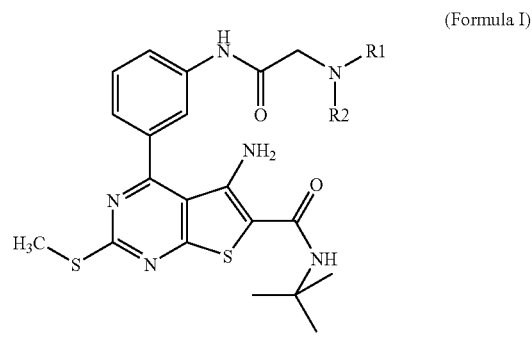

(Formula I)

or a pharmaceutically acceptable salt thereof, wherein N(R1)R2 are joined in a (2-6C)heterocycloalkyl ring.

The most preferred compounds are tert-butyl 5-amino-2-methylthio-4-(3-(2-(azetidin-1-yl)-acetamido)-phenyl)-thieno[2,3-d]pyrimidine-6-carboxamide; tert-butyl 5-amino-2-methylthio-4-(3-(2-(morpholin-4-yl)-acetamido)-phenyl)-thieno[2,3-d]pyrimidine-6-carboxamide; tert-butyl 5-amino-2-methylthio-4-(3-(2-(thiomorpholin-4-yl)-acetamido)-phenyl)-thieno[2,3-d]pyrimidine-6-carboxamide; tert-butyl 5-amino-2-methylthio-4-(3-(2-(piperidin-1-yl)-acetamido)-phenyl)-thieno[2,3-d]pyrimidine-6-carboxamide; tert-butyl 5-amino-2-methylthio-4-(3-(2-(pyrrolidin-1-yl)-acetamido)-phenyl)-thieno[2,3-d]pyrimidine-6-carboxamide and tert-butyl 5-amino-2-methylthio-4-(3-(2-(piperazin-1-yl)-acetamido)-phenyl)-thieno[2,3-d]pyrimidine-6-carboxamide.

The term joined in a (2-6C)heterocycloalkyl ring in the definition of Formula I, means that R1 and R2 together with the nitrogen atom to which they are bonded form a ring having 2-6 carbon atoms, optionally containing one or more heteroatoms selected from N, O and/or S. Examples of such rings are azetidine, pyrrolidine, piperidine, piperazine, morpholine and thiomorpholine.

It has been shown that compounds of the above mentioned formula I show agonistic LH and FSH activity. In an in vitro bioassay using CHO cells stably transfected with the human LH or FSH receptor, respectively, the $EC_{50}$ with regard to the LH receptor was found to be less than $5.10^{-8}$ M whereas with regard to the FSH receptor the $EC_{50}$ was less than $10^{-5}$M. Typically the FSH activity ranges from an activity of about 1% of the LH agonist stimulation to about 10% of the LH agonist stimulation.

The invention further resides in a pharmaceutical composition comprising a thieno[2,3-d]pyrimidine derivative compound or salts thereof having the general formula I.

Thus, the compounds according to the invention can be used in therapy. A further aspect of the invention resides in the use of a thieno[2,3-d]pyrimidine compound having the general formula I for the manufacture of a medicament for the control of fertility, more preferably induction of ovulation. The present compounds are used to activate both the LH and FSH receptors. The compound of the present invention can be used therefore in a method to treat females with fertility problems.

For therapeutic use, salts of the compounds of formula I are those wherein the counterion is pharmaceutically acceptable. However, acid addition salts of bases according to formula I, may also find use, for example, in the preparation or purification of a pharmaceutically acceptable compound. All salts, whether pharmaceutically acceptable or not, are included within the ambit of the present invention.

Examples of acid addition salts include those derived from mineral acids such as hydrochloric acid, phosphoric acid, sulphuric acid, preferably hydrochloric acid, and organic acids like citric acid, tartaric acid, acetic acid, lactic acid, maleic acid, malonic acid, fumaric acid, glycolic acid, succinic acid, and the like.

Suitable administration routes for the compounds of formula I or pharmaceutically acceptable salts thereof, also referred to herein as the active ingredient are intramuscular injections, subcutaneous injections, intravenous injections or intraperitoneal injections, oral and intranasal administration. Preferably, the compounds may be administered orally. The exact dose and regimen of administration of the active ingredient, or a pharmaceutical composition thereof, will necessarily be dependent upon the therapeutic effect to be achieved (treatment of infertility; contraception), and may vary with the particular compound, the route of administration, and the age and condition of the individual subject to whom the medicament is to be administered.

In general, parenteral administration requires lower dosages than other methods of administration which are more dependent upon adsorption. However, a dosage for humans preferably contains 0.0001-25 mg per kg body weight. The desired dose may be presented as one dose or as multiple subdoses administered at appropriate intervals throughout the day. In case of female recipients, doses may be administered at appropriate daily intervals throughout the menstrual cycle for follicular support or as a single dose for ovulation induction. The dosage as well as the regimen of administration may differ between a female and a male recipient.

In case of in vitro or ex vivo applications, like in IVF applications, the compounds of the inventions are to be used in the incubation media in a concentration of approximately 0.01-5 µg/ml.

The present invention thus also relates to pharmaceutical compositions comprising a thieno[2,3-d]pyrimidine compound according to formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurized aerosols, nebulisers or insufflators.

The thieno[2,3-d]pyrimidine compounds of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303, 306 (AKZO N.V.).

Thus, the compounds according to the present invention can be used for the same clinical purposes as the native LH, with the advantage that they possess FSH activity, display altered stability properties and can be administered differently.

The compounds of the present invention, represented by formula (I) can generally be prepared by nucleophilic substitution of halides (II) wherein Q=Cl or Br with (cyclic) secondary amines of formula (III) in an appropriate solvent such as N,N-dimethylformamide or THF at room temperature in the presence of a tertiary base such as N,N-diisopropylethylamine (DIPEA).

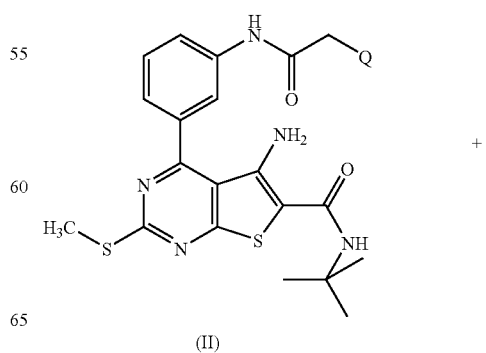

(II)

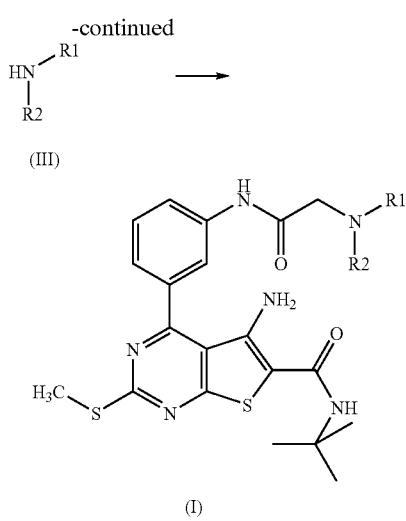

Derivatives of formula (II) wherein Q=Cl or Br can be prepared by regioselective acylation of meta aniline derivative (V) with acyl chlorides of type (IV), wherein Q=Cl or Br in the presence of a tertiary base such as N,N-diisopropylethylamine in a suitable solvent such as dichloromethane or THF.

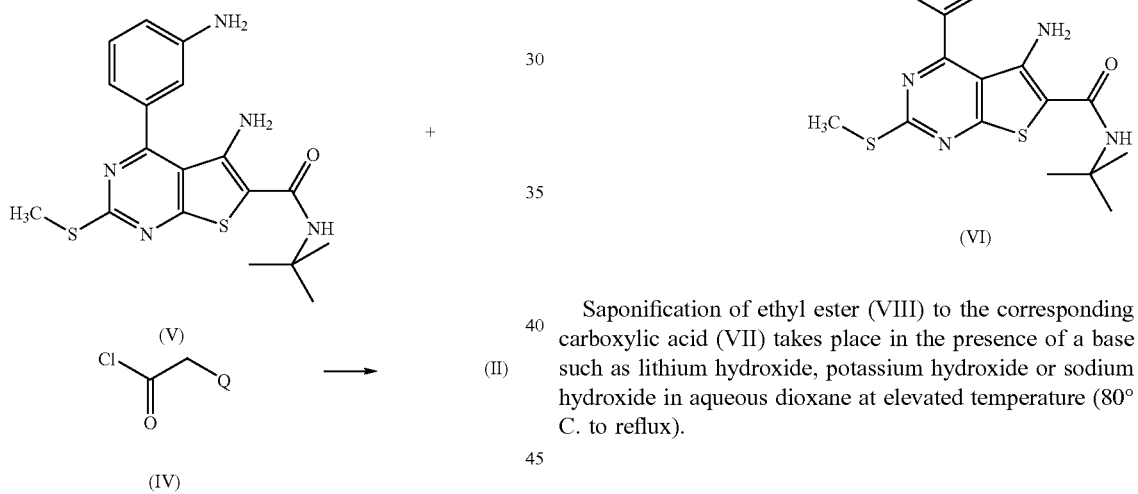

Compound (V) is accessible by art-known reduction of the nitro function in derivative (VI) using an appropriate reducing agent such as tin(II) chloride in a protic solvent such as ethanol in the presence of hydrochloric acid at elevated temperature (J. Heilbron, J: Chem. Soc, 1279 (1940)).

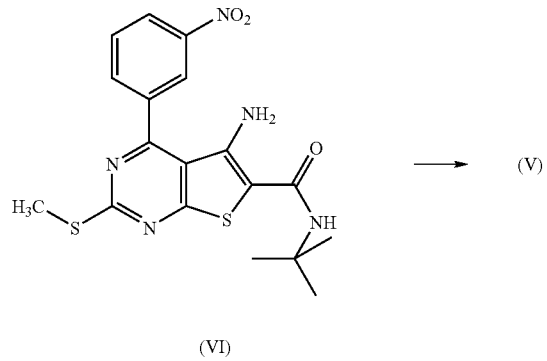

Thienopyrimidine (VI) can be prepared by condensation of carboxylic acid (VII) with tert-butyl amine under the influence of a coupling agent such as O-(benzotriazol-1-yl)-N,N,N',N'-tetramethyluronium tetrafluoroborate (TBTU) or bromotripyrrolidinophosphonium hexafluorophosphate (PyBrOP) and a tertiary base, e.g. N,N-diisopropylethylamine.

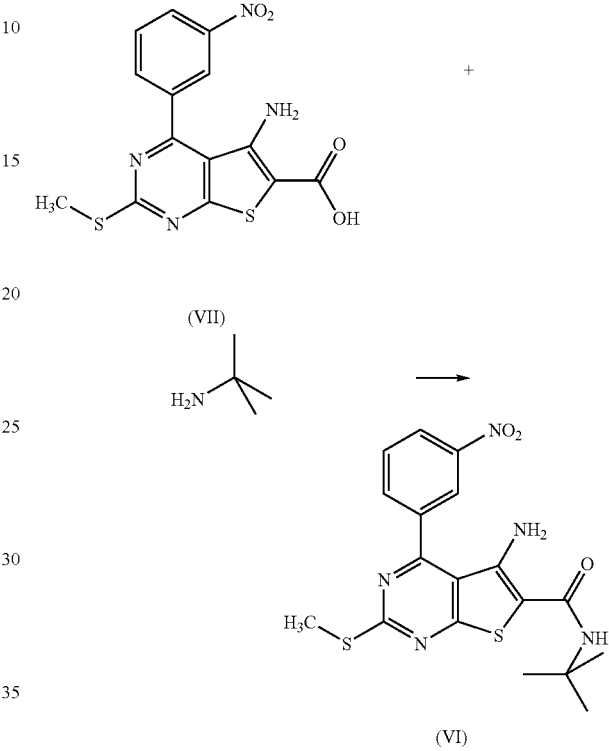

Saponification of ethyl ester (VIII) to the corresponding carboxylic acid (VII) takes place in the presence of a base such as lithium hydroxide, potassium hydroxide or sodium hydroxide in aqueous dioxane at elevated temperature (80° C. to reflux).

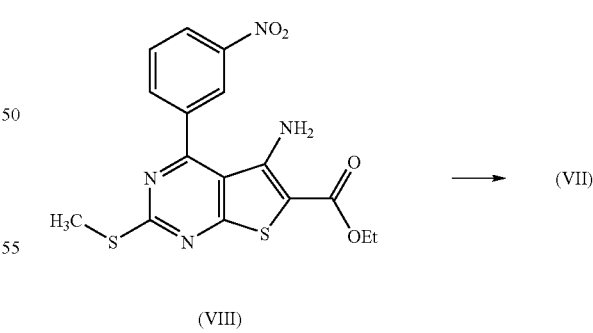

Bicycle (VIII) is formed by substitution of chloride (X) with ethyl mercaptoacetate under the agency of N,N-diisopropylethylamine, followed by base-catalyzed ring-closure of the intermediate thioether (IX). This type of thieno[2,3-d]pyrimidine ring formations has been described in: S. A. Abdel-Hady, M. A. Badawy, Y. A. Ibrahim, Sulfur Lett. 9, 101 (1989) and S. Tumkevicius, Liebigs Ann., 1703 (1995).

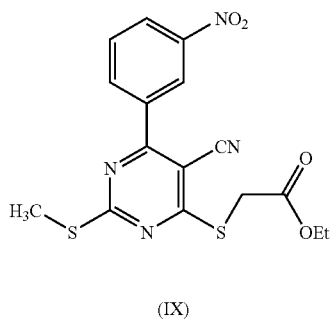

(IX)

Suitable conditions for the cyclization reaction are sodium ethoxide in ethanol or N,N-diisopropylethylamine in toluene/ethanol (1/1, v/v) at reflux temperature.

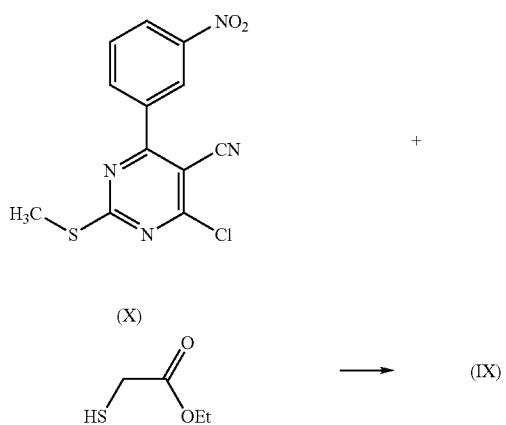

The requisite chloroimine (X) can be synthesized following literature procedures as described for example by A. A. Santilli, D. H. Kim and S. V. Wanser, J. Heterocycl. Chem. 8, 445, 1971. According to this procedure, lactam (XI) is treated with $POCl_3$ at elevated temperature (80° C. to reflux) to give chloride (X). The addition of an appropriate solvent, e.g. dioxane, and/or the addition of either $PCl_5$ or NN-dimethylaniline to the reaction mixture may result in shorter reaction times and higher yields of chloride (X).

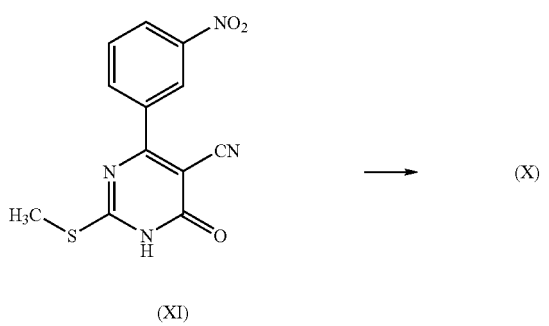

An appropriate route towards lactam (XI) comprises the multicomponent condensation of ethyl cyanoacetate with 3-nitro-benzaldehyde and S-methyl isothiourea in ethanol under the agency of a base such as potassium carbonate at elevated temperature (60° C.).

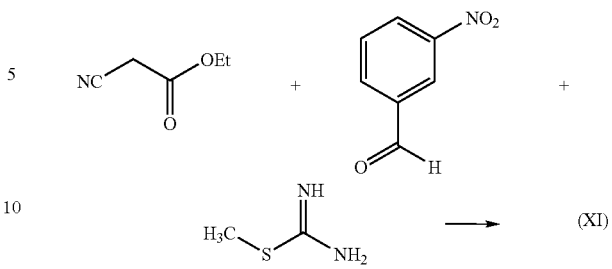

Related procedures have been disclosed in: S. Kambe, K. Saito and H. Kishi, Synthesis, 287 (1979); A. M. Abd-Elfattah, S. M. Hussain and A. M. El-Reedy, Tetrahedron 39, 3197 (1983); S. M. Hussain, A. A. El-Barbary and S. A. Mansour, J. Heterocycl. Chem. 22, 169 (1985).

Methods to determine receptor binding as well as in vitro and in vivo assays to determine biological activity of gonadotropins are well known. In general, expressed receptor is contacted with the compound to be tested and binding or stimulation or inhibition of a functional response is measured.

To measure a functional response isolated DNA encoding the LH or the FSH receptor gene, preferably the human receptor, is expressed in suitable host cells. Such a cell might be the Chinese Hamster Ovary cell, but other cells are also suitable.

Preferably the cells are of mammalian origin (Jia et al, Mol.Endocrin., 5, 759-776, 1991).

Methods to construct recombinant LH or FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively isolated cell membranes containing the expressed receptor may be used to measure binding of compound.

For measurement of binding radioactively or fluorescently labeled compounds may be used. As reference compound human recombinant LH or FSH can be used. In the alternative also competition binding assays can be performed.

Another assay involves screening for LH or FSH receptor agonist compounds by determining stimulation of receptor mediated cAMP accumulation. Thus, such a method involves expression of the receptor on the cell surface of a host cell and exposing the cell to the test compound. The amount of cAMP is than measured. The level of cAMP will be reduced or increased, depending on the inhibitory or stimulating effect of the test compound upon binding to the receptor.

In addition to direct measurement of e.g. cAMP levels in the exposed cell, cells can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch, Himmler, A and Czernilofsky, A. P., Curr.Opin.Biotechnol.6, 574 (1995).

For selecting active compounds on the LH or FSH receptor, testing at $10^{-5}$ M must result in an activity of more than 20% of the maximal activity when LH or FSH is used as a reference. Another criterion might be the $EC_{50}$ value, which must be <$10^{-5}$ M, preferably <$10^{-7}$ M.

The skilled artisan will recognize that desirable $EC_{50}$ values are dependent on the compound tested. For example, a compound with an $EC_{50}$, which is less than 10-5 M is generally, considered a candidate for drug selection. Preferably this value is lower than $10^{-7}$ M. However, a compound which has a higher $EC_{50}$, but is selective for the particular receptor, may be even a better candidate.

Screening for LH receptor agonistic compounds can also be performed by using a mouse Leydig cell bioassay (Van Damme, M., Robersen, D. and Diczfalusy, E., Acta Endocrinol. 77: 655-671 (1974), Mannaerts, B., Kloosterboer, H. and Schuurs, A., Neuroendocrinology of reproduction. R. Rolland et al. Eds., Elsevier Science Publishers B.V., 49-58 (1987)). In this assay, stimulation of LH receptor mediated testosterone production can be measured in Leydig cells isolated from male mice.

FSH agonistic activity of compounds can also be determined in an ex vivo model using cultured mouse follicles according to Nayudu, P. and Osborn, S. (J. Reproduction and Fertility 95, 349-362 (1992)). Therefore, mouse ovarian follicles are isolated and cultured in the presence of FSH agonistic compounds to induce follicular growth. Measurements of follicular diameter and estradiol in the culture medium are indicative for follicular growth.

To measure LH in vivo activity of compounds, ovulation induction in immature mice can be studied. In this assay immature female mice are primed with urinary FSH and approximately 48 hours later treated with a LH agonistic compound. The animals are killed after LH agonist treatment and the number of ova in the oviduct is microscopically assessed.

To measure FSH in vivo activity of compounds immature female rats are treated at 0, 8, 24 and 32 hours with a FSH agonistic compound to induce follicular growth. At 52 hours after the start of the experiment the animals are injected with hCG to induce ovulation. The animals are killed 72 hours after the start of the experiment and the number of ova in the oviduct is microscopically assessed. In addition ovarian weight is determined.

The compounds of the present invention can be applied clinically in those regimens where now LH or hCG is used. These include LH substitution among subjects with hypogonadal hypogonadism either male or female, midcycle administration to induce ovulation (ovulation induction (OI) or controlled hyperstimulation (COH) or stimulation of the corpus luteum.

The following examples are illustrative for the invention and should in no way be interpreted as limiting the scope of the invention.

EXAMPLES

Example 1 tert-Butyl 5-amino-2-methylthio-4-(3-(2-(azetidin-1-yl)-acetamido)-phenyl)-thieno[2,3-d]pyrimidine-6-carboxamide (a). 5-Cyano-4-(3-nitrophenyl)-2-methylthio-6-oxopyrimidine A mixture of S-methylisothiourea sulfate (69.0 g), 3-nitrobenzaldehyde (75.0 g), ethyl cyanoacetate (56.0 ml) and potassium carbonate (72.5 g) in abs. EtOH (1500 ml) was stirred at 60° C. for 16 h. The reaction mixture was cooled to 0° C. in an ice bath. The resulting precipitate was filtered off, washed with abs. EtOH and dissolved in hot water (100° C.). The solution was cooled to room temperature, acidified with 2N HCl to pH 2 and cooled to 0° C. in an ice bath. The resulting precipitate was filtered off and washed with ice water. Residual water in the precipitate was removed by coevaporation with 1,4-dioxane.

Yield: 54.0 mg. MS-ESI: $[M+H]^+$=289.0 TLC: $R_f$=0.3, silica gel, DCM/MeOH=9/1 (v/v).

(b). 6-Chloro-5-cyano-4-(3-nitrophenyl)-2-methylthio-pyrimidine $POCl_3$ (100 ml) was added to a stirred solution of 5-cyano-4-(3-nitrophenyl)-2-methylthio-6-oxopyrimidine (example 1(a), 25.0 g) in dry 1,4-dioxane (300 ml). After 3 h at 90° C., the mixture was cooled to room temperature and concentrated under reduced pressure. The residue was dissolved in 1,4-dioxane (100 ml) and the resulting solution was cooled to 0° C. Ice water was cautiously added. The resulting precipitate was filtered off and washed with water. Residual water in the precipitate was removed by coevaporation with 1,4-dioxane.

Yield: 26.0 g. MS-ESI: $[M+H]^+$=307.0 TLC: $R_f$=0.5, silica gel, heptane/EtOAc=3/2 (v/v).

(c). Ethyl 5-cyano-4-(3-nitrophenyl)-2-methylthio-6-(ethoxycarbonylmethylthio)-pyrimidine DIPEA (15.7 ml) was added to a stirred solution of ethyl 2-mercaptoacetate (9.3 ml) and 6-chloro-5-cyano-4-(3-nitrophenyl)-2-methylthio-pyrimidine (example 1(b), 26.0 g) in a mixture of EtOH (250 ml) and DCM (250 ml). After 1 h at room temperature, 0.1N aq. HCl (500 ml) was added to the mixture which was then extracted with DCM (3*500 ml), dried ($MgSO_4$) and concentrated under reduced pressure.

Yield: 28.0 g MS-ESI: $[M+H]^+$=390.4 TLC: $R_f$=0.5, silica gel, heptane/EtOAc=3/2 (v/v).

(d). Ethyl 5-amino-4-(3-nitrophenyl)-2-methylthio-thieno[2,3-d]pyrimidine-6-carboxylate A mixture of ethyl 5-cyano-4-(3-nitrophenyl)-2-methylthio-6-(ethoxycarbonylmethylthio)-pyrimidine (example 1(c), 28.0 g) and DIPEA (30 ml) in a mixture of toluene (150 ml) and EtOH (150 ml) was stirred at reflux temperature (100° C.) for 16 h. The mixture was then cooled to room temperature and concentrated under reduced pressure. Residual DIPEA was removed by coevaporation with toluene.

Yield: 28.0 g MS-ESI: [M+H]$^+$=391.2 TLC: R$_f$=0.6, silica gel, heptane/EtOAc=3/2 (v/v).

(e). Ethyl 5-amino-4-(3-aminophenyl)-2-methylthio-thieno[2,3-d]pyrimidine-6-carboxylate EtOH (400 ml) was added to a mixture of ethyl 5-amino-4-(3-nitrophenyl)-2-methylthio-thieno[2,3-d]pyrimidine-6-carboxylate (example 1(d), 28.0 g), concentrated aq. HCl (15 ml) and tin (II) chloride (41.0 g) in 1,4-dioxane (400 ml). The mixture was stirred at 90° C. for 16 h. The mixture was then cooled to room temperature and concentrated under reduced pressure. The residue was suspended, in EtOAc (1000 ml). 4N aq. NaOH was added to obtain a pH of 10-11. The mixture was vigourously stirred and the organic layer was separated, dried (MgSO$_4$) and concentrated under reduced pressure.

Yield: 21.0 g MS-ESI: [M+H]$^+$=361.0 TLC: R$_f$=0.6, silica gel, heptane/EtOAc=3/2 (v/v).

(f). 5-Amino-4-(3-aminophenyl)-2-methylthio-thieno[2,3-d]pyrimidine-6-carboxylic acid Potassium hydroxide (32.4 g) was added to a solution of ethyl 5-amino-4-(3-aminophenyl)-2-methylthio-thieno[2,3-d]pyrimidine-6-carboxylate (example 1(e), 21.0 g) in a mixture of 1,4-dioxane (300 ml) and water (100 ml). After 16 h at 90° C., the mixture was cooled to 10° C. and 2N aq. citric acid (300 ml) was added under vigourous stirring. The resulting precipitate was filtered off, washed with water (180 ml) and dried in vacuo.

Yield: 14.0 g MS-ESI: [M+H]$^+$=333.0 TLC: R$_f$=0.5, silica gel, DCM/MeOH=9/1 (v/v).

(g). tert-Butyl 5-amino-4-(3-aminophenyl)-2-methylthio-thieno[2,3-d]pyrimidine-6-carboxamide TBTU (16.1 g) was added to a solution of 5-amino-4-(3-aminophenyl)-2-methylthio-thieno[2,3-d]pyrimidine-6-carboxylic acid (example 1(f), 14.0 g), DIPEA (17.4 ml) and tert-butylamine (7.3 g) in DCM/DMF (1/1, v/v, 250 ml). After 3 h at room temperature, the mixture was washed with sat. aq. NaHCO$_3$ (3*100 ml), 0.1 N aq. HCl (100 ml) and water (100 ml). The organic layer was concentrated under reduced pressure. The crude product was purified by crystallization from warm abs. EtOH (300 ml).

Yield: 10.5 g MS-ESI: [M+H]$^+$=388.2 HPLC: R$_t$=30.72 min, Luna C-18(2), 5 μm, 250*2.0 mm, detection UV=210 nm, oven temperature=40° C., flow=0.25 ml/min, eluent water/ACN/MeOH=90/9.5/0.5 to 0/95/5, run time=50 min.

(h). tert-Butyl 5-amino-2-methylthio-4-(3-(2-bromoacetamido)-phenyl)-thieno[2,3-d]pyrimidine-6-carboxamide Bromoacetylchloride (615 mg) was added to a solution of tert-butyl 5-amino-2-methylthio-4-(3-aminophenyl)-thieno[2,3-d]-pyrimidine-6-carboxamide (example 1(g), 1.08 g) and DIPEA (2.43 ml) in dry DCM (20 ml). After 3 h at room temperature, the mixture was diluted with DCM, washed with sat. aq. NaHCO$_3$, dried (MgSO$_4$) and concentrated under reduced pressure. The crude product was purified by chromatography on silica gel using heptane/EtOAc=3/2 (v/v) as eluent.

Yield: 910 mg MS-ESI: [M+H]$^+$=510.2 TLC: R$_f$=0.3, silica gel, heptane/EtOAc=3/2 (v/v).

(i). tert-Butyl 5-amino-2-methylthio-4-(3-(2-(azetidin-1-yl)-acetamido)-phenyl)-thieno[2,3-d]pyrimidine-6-carboxamide tert-Butyl 5-amino-4-(3-(2-bromoacetamido)-phenyl)-2-methylthio-thieno[2,3-d]pyrimidine-6-carboxamide (example 1(h), 91 mg) was added to a solution of azetidine hydrochloride (120 mg) and N,N-diisopropylethylamine (0.25 ml) in DCM (5 ml). After 16 h at room temperature, the mixture was washed with sat. aq. NaHCO$_3$, dried (MgSO$_4$) and concentrated under reduced pressure. The crude product was purified by HPLC using a Luna C-18 column with the following gradient: 0.1% aq.TFA+10% aq. ACN/ACN=90/10 to 10/90 in 30 min. The title compound was then lyophilized from water with 0.1% TFA.

Yield: 56 mg (TFA-salt) MS-ESI: [M+H]$^+$=485.2 HPLC: R$_t$=13.45 min, column Luna C-18(2), 3 μm, 100*2.0 mm, detection UV=210 nm, oven temperature=40° C., flow=0.25 ml/min, eluent phosphate buffer 50 mM pH 2.1/water/ACN=10/70/20 to 10/10/80 (v/v), run time=20 min.

Example 2 tert-Butyl 5-amino-2-methylthio-4-(3-(2-(morpholin-4-yl)-acetamido)-phenyl)-thieno[2,3-d]pyrimidine-6-carboxamide Morpholine (5:0 ml) was added to a solution of tert-butyl 5-amino-4-(3-(2-bromoacetamido)-phenyl)-2-methylthio-thieno[2,3-d]pyrimidine-6-carboxamide (example 1(h), 1.0 g) in THF (50 ml). After 16 h at room temperature, the mixture was concentrated under reduced pressure. The residue was purified by column chromatography on silica gel using DCM/MeOH=9/1 as eluent. The crude product was further purified by HPLC using a Luna C-18 column with the following gradient: 0.1% aq. TFA/water/ACN=3/97/0 to 3/7/90 in 30 min. The pure title compound was lyophilized from a mixture of 0.1% aq. TFA and water.

Yield: 215 mg (TFA-salt) MS-ESI: [M+H]$^+$=515.2 HPLC: R$_t$=20.62 min, Luna C-18 (2), 5 μm, 150*2 mm, detection UV=210 nm, oven temperature=40° C., flow=0.25 ml/min, eluent phosphate buffer 50 mM pH 2.1/water/ACN/MeOH=10/72/17/1 to 10/18/68/4 (v/v), run time=40 min.

Example 3 tert-Butyl 5-amino-2-methylthio-4-(3-(2-(thiomorpholin-4-yl)-acetamido)-phenyl)-thieno[2,3-d]pyrimidine-6-carboxamide Thiomorpholine (2.16 ml) was added to a solution of tert-butyl 5-amino-2-methylthio-4-(3-(2-bromoacetamido)-phenyl)-thieno[2,3-d]pyrimidine-6-carboxamide (example 1(h), 1.09 g) in DCM (50 ml). After 16 h at room temperature, the mixture was diluted with DCM, washed with sat. aq. NaHCO$_3$, dried (MgSO$_4$) and concentrated under reduced pressure. The crude product was purified by HPLC using a Luna C-18 column with the following gradient: 0.1% aq. TFA+10% aq. ACN/ACN=100/0 to 10/90 in 30 min. The pure title compound was lyophilized from water acidified with aq. 1N HCl.

Yield: 816 mg MS-ESI: $[M+H]^+=531.2$ HPLC:$R_t=14.72$ min, column Luna C-18(2), 3 μm, 100*2 mm, detection UV=210 nm+254 nm, oven temperature=40° C., flow=0.25 ml/min, eluent phosphate buffer 50 mM pH 2.1/water/ACN/MeOH=10/72/17/1 to 10/18/68/4(v/v), run time=20 min.

Example 4 tert-Butyl 5-amino-2-methylthio-4-(3-(2-(piperidin-1-yl)-acetamido)-phenyl)-thieno[2,3-d]pyrimidine-6-carboxamide Piperidine (3.0 ml) was added to a solution of tert-butyl 5-amino-4-(3-(2-bromoacetamido)-phenyl)-2-methylthio-thieno[2,3-d]pyrimidine-6-carboxamide (example 1(h), 1.0 g) in $CH_2Cl_2$ (50 ml). After 16 h at room temperature, the mixture was concentrated under reduced pressure. The residue was purified by column chromatography on silica gel using DCM/MeOH=9/1 as eluent. The crude product was further purified by HPLC using a Luna C-18 column with the following gradient: 0.1% aq. TFA/ACN=100/0 to 10/90 in 30 min. The pure title compound was lyophilized from a mixture of 0.1% aq. TFA and water.

Yield: 851 mg (TFA-salt) MS-ESI: $[M+H]^+=513.2$ HPLC: Rt=37.3 min, Luna C-18 (2), 5 μm, 150*2 mm, detection UV=210 nm, oven temperature=40° C., flow=0.25 ml/min, eluent phosphate buffer 50 mM pH 2.1/water/ACN=20/60/20 to 20/0/80 (v/v), run time=40 min.

Example 5 tert-Butyl 5-amino-2-methylthio-4-(3-(2-(pyrrolidin-1-yl)-acetamido)-phenyl)-thieno[2,3-d]pyrimidine-6-carboxamide Pyrrolidine (3.0 ml) was added to a solution of tert-butyl 5-amino-4-(3-(2-bromoacetamido)-phenyl)-2-methylthio-thieno[2,3-d]pyrimidine-6-carboxamide (example 1(h), 1.0 g) in $CH_2Cl_2$ (50 ml). After 16 h at room temperature, the mixture was concentrated under reduced pressure. The residue was purified by column chromatography on silica gel using DCM/MeOH=9/1 as eluent. The crude product was further purified by HPLC using a Luna C-18 column with the following gradient: 0.1% aq. TFA/ACN=100/0 to 10/90 in 30 min. The pure title compound was lyophilized from a mixture of 0.1% aq. TFA and water.

Yield: 616 mg (TFA-salt) MS-ESI: $[M+H]^+=499.2$ HPLC: Rt=37.5 min, Luna C-18 (2), 5 μm, 150*2 mm, detection UV=210 nm, oven temperature=40° C., flow=0.25 ml/min, eluent phosphate buffer 50 mM pH 2.1/water/ACN=20/60/20 to 20/0/80 (v/v), run time=40 min.

Example 6 tert-Butyl 5-amino-2-methylthio-4-(3-(2-(piperidin-1-yl)-acetamido)-phenyl)-thieno[2,3-d]pyrimidine-6-carboxamide Piperazine (2.5 g) was added to a solution of tert-butyl 5-amino-4-(3-(2-bromoacetamido)-phenyl)-2-methylthio-thieno[2,3-d]pyrimidine-6-carboxamide (example 1(h), 1.0 g) in $CH_2Cl_2$ (50 ml). After 16 h at room temperature, the mixture was concentrated under reduced pressure. The residue was purified by column chromatography on silica gel using DCM/MeOH=7/1 as eluent. The crude product was further purified by HPLC using a Luna C-18 column with the following gradient: 0.1% aq. TFA/ACN=100/0 to 10/90 in 30 min. The pure title compound was lyophilized from a mixture of 0.1% aq. TFA and water.

Yield: 766 mg (bis TFA-salt) MS-ESI: $[M+H]^+=514.4$ HPLC: Rt=33.7 min, Luna C-18 (2), 5 μm, 150*2 mm, detection UV=210 nm, oven temperature=40° C., flow=0.25 ml/min, eluent phosphate buffer 50 mM pH 2.1/water/ACN=20/60/20 to 20/0/80 (v/v), run time=40 min.

Example 7

CHO-LH and CHO—FSH in vitro Bioactivity

LH agonistic activity of compounds were tested in Chinese Hamster Ovary (CHO) cells stably transfected with the human receptor and cotransfected with a cAMP responsive element (CRE)/promotor directing the expression of a firefly luciferase reporter gene. Binding of ligand to the Gs-coupled LH receptor will result in an increase of cAMP, which in turn will induce an increased transactivation of the luciferase reporter construct. The luciferase signal was quantified using a luminescence counter. For test compounds, $EC_{50}$ values (concentration of test compound causing half-maximal (50%) stimulation) were calculated. For that purpose the software program GraphPad PRISM, version 3.0 (GraphPad software Inc., San Diego) was used.

In a similar way FSH agonistic activity of compounds was tested in CHO cells transfected with the luciferase reporter gene and the human FSH receptor. Results are shown in Table 1.

In vivo Bioactivity

To measure in vivo activity of LH/FSH receptor agonistic compounds ovulation induction in immature mice was studied. In this assay immature female mice were primed with urinary FSH (Humegon 12.5 IU/animal). Approximately 48 hours later the animals were treated with a LH/FSH agonistic compound at a dose-level of 50 mg/kg. The animals were killed 24 hours after LH/FSH agonist treatment and the number of ova in the oviduct was microscopically assessed. Results are shown in Table 1.

TABLE 1

| Example no. | Name | EC50 CHO LHR (M) | EC50 CHO FSHR (M) | no. animals tested | mean no. of ova (50 mg/kg p.o.) |
|---|---|---|---|---|---|
| 1 | tert-Butyl 5-amino-2-methylthio-4-(3-(2-(azetidin-1-yl)-acetamido)-phenyl)-thieno[2,3-d]pyrimidine-6-carboxamide | 3.86E–09 | 4.62E–07 | 15 | 1.6 |
| 2 | tert-Butyl 5-amino-2-methylthio-4-(3-(2-(morpholin-4-yl)-acetamido)-phenyl)-thieno[2,3-d]pyrimidine-6-carboxamide | 2.24E–09 | 4.20E–08 | 10 | 9.3 |

TABLE 1-continued

| Example no. | Name | EC50 CHO LHR (M) | EC50 CHO FSHR (M) | no. animals tested | mean no. of ova (50 mg/kg p.o.) |
|---|---|---|---|---|---|
| 3 | tert-Butyl 5-amino-2-methylthio-4-(3-(2-(thiomorpholin-4-yl)-acetamido)-phenyl)-thieno[2,3-d]pyrimidine-6-carboxamide | 8.03E−09 | 1.04E−06 | 10 | 19.8 |
| 4 | tert-Butyl 5-amino-2-methylthio-4-(3-(2-(piperidin-1-yl)-acetamido)-phenyl)-thieno[2,3-d]pyrimidine-6-carboxamide | 6.63E−09 | 2.01E−07 | | |
| 5 | tert-Butyl 5-amino-2-methylthio-4-(3-(2-(pyrrolidin-1-yl)-acetamido)-phenyl)-thieno[2,3-d]pyrimidine-6-carboxamide | 6.68E−09 | 4.80E−07 | | |
| 6 | tert-Butyl 5-amino-2-methylthio-4-(3-(2-(piperazin-1-yl)-acetamido)-phenyl)-thieno[2,3-d]pyrimidine-6-carboxamide | 3.17E−09 | 1.50E−07 | | |

The invention claimed is:

1. A thieno[2,3-d]pyrimidine according to

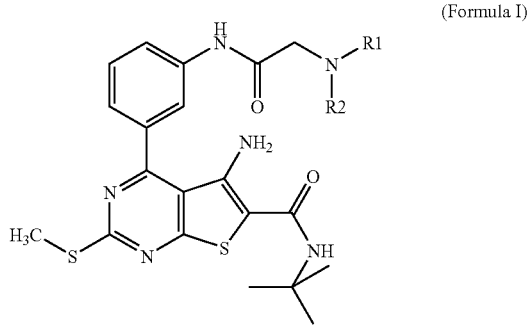

(Formula I)

formula I, or a pharmaceutically acceptable salt thereof, wherein R1 and R2 together with the nitrogen atom to which they are bonded form a ring having 2-6 carbon atoms, optionally containing one or more heteroatoms selected from N, O and/or S.

2. A compound selected from the group consisting of tert-butyl 5-amino-2-methylthio-4-(3-(2-(azetidin-1-yl)-acetamido)-phenyl)-thieno[2,3-d]pyrimidine -6-carboxamide; tert-butyl 5-amino-2-methylthio-4-(3-(2-(morpholin-4-yl)-acetamido) -phenyl)-thieno[2,3-d]pyrimidine-6-carboxamide; tert-butyl 5-amino-2-methylthio -4-(3-(2-(thiomorpholin-4-yl)-acetamido)-phenyl)-thieno[2,3-d]pyrimidine-6-carboxamide; tert-butyl 5-amino-2-methylthio-4-(3-(2-(piperidin-1-yl)-acetamido)-phenyl)-thieno [2,3-d]pyrimidine-6-carboxamide; tert-butyl 5-amino-2-methylthio-4-(3-(2-(pyrrolidin-1-yl)-acetamido)-phenyl)-thieno[2,3-d]pyrimidine-6-carboxamide and tert-butyl 5-amino-2-methylthio -4-(3-(2-(piperazin-1-yl)-acetamido)-phenyl)-thieno[2,3-d]pyrimidine-6-carboxamide or a pharmaceutically acceptable salt thereof.

3. A pharmaceutical composition, comprising:
the thieno[2,3-d]pyrimidine compound according to claim 1 or a pharmaceutically acceptable salt thereof, and a pharmaceutically acceptable auxiliary.

4. A method to treat fertility disorders in patients in need of luteinizing hormone and follicle stimulating hormone treatment, comprising:
administering an effective amount of the compound or pharmaceutically acceptable salt thereof according to claim 1.

5. A pharmaceutical composition, comprising:
the thieno[2,3-d]pyrimidine compound according to claim 2 or a pharmaceutically acceptable salt thereof, and a pharmaceutically acceptable auxiliary.

6. A method to treat fertility disorders in patients in need of luteinizing hormone and follicle stimulating hormone treatment, comprising:
administering an effective amount of the compound or a pharmaceutically acceptable salt thereof according to claim 2.

7. The method of claim 4, wherein the fertility disorder is selected from the group consisting of hypogonadism and male infertility.

8. The method of claim 4, wherein the fertility disorder is hypogonadism.

9. The method of claim 4, wherein the fertility disorder is male infertility.

10. The method of claim 6, wherein the fertility disorder is selected from the group consisting of hypogonadism and male infertility.

11. The method of claim 6, wherein the fertility disorder is hypogonadism.

12. The method of claim 6, wherein the fertility disorder is male infertility.

13. A method for treating infertility by ovulation induction or by controlled hyperstimulation, the method comprising administering an effective amount of the compound or pharmaceutically acceptable salt thereof according to claim 1.

14. A method for treating infertility by ovulation induction or by controlled hyperstimulation, the method comprising administering an effective amount of the compound or pharmaceutically acceptable salt thereof according to claim 2.

* * * * *